US011430566B2

(12) United States Patent
Ochoa et al.

(10) Patent No.: US 11,430,566 B2
(45) Date of Patent: Aug. 30, 2022

(54) SCANNER DEVICES FOR IDENTIFYING AND STORING INFORMATION EMITTED BY IMPLANTED MEDICAL DEVICES

(71) Applicants: Leandro Estevan Ochoa, Spring, TX (US); Joel Ochoa, Spring, TX (US)

(72) Inventors: Leandro Estevan Ochoa, Spring, TX (US); Joel Ochoa, Spring, TX (US)

( * ) Notice: Subject to any disclaimer, the term of this patent is extended or adjusted under 35 U.S.C. 154(b) by 199 days.

(21) Appl. No.: 16/591,955

(22) Filed: Oct. 3, 2019

(65) Prior Publication Data

US 2020/0111567 A1  Apr. 9, 2020

Related U.S. Application Data

(60) Provisional application No. 62/740,824, filed on Oct. 3, 2018.

(51) Int. Cl.
| | |
|---|---|
| *G16H 40/40* | (2018.01) |
| *A61B 5/00* | (2006.01) |
| *H01M 10/48* | (2006.01) |
| *G01R 31/382* | (2019.01) |
| *G01R 31/36* | (2020.01) |

(52) U.S. Cl.
CPC ............ *G16H 40/40* (2018.01); *A61B 5/686* (2013.01); *G01R 31/3648* (2013.01); *G01R 31/382* (2019.01); *H01M 10/48* (2013.01); *A61B 2560/0276* (2013.01)

(58) Field of Classification Search
None
See application file for complete search history.

(56) References Cited

U.S. PATENT DOCUMENTS

| | | | |
|---|---|---|---|
| 7,191,013 B1* | 3/2007 | Miranda | H01Q 1/2216 607/60 |
| 7,240,833 B2 | 7/2007 | Zarembo | |
| 9,878,167 B1 | 1/2018 | He et al. | |
| 2005/0065815 A1 | 3/2005 | Mazar et al. | |
| 2006/0235488 A1* | 10/2006 | Nycz | A61B 90/90 607/60 |
| 2007/0018810 A1* | 1/2007 | Smythe | A61B 5/0031 340/539.12 |
| 2007/0041626 A1* | 2/2007 | Weiss | G06Q 10/10 382/131 |

(Continued)

FOREIGN PATENT DOCUMENTS

WO  WO2003077994 A1  9/2003

*Primary Examiner* — Brent A. Fairbanks

(57) ABSTRACT

Embodiments disclosed herein convey scanner devices and methods for identifying and storing information emitted by implanted medical devices. In some embodiments, the scanner device includes at least one display, input device, and transceiver all communicatively coupled via at least one control circuit. The control circuit is configured to transmit, via the transceiver, a first interrogating signal to a medical device implanted within a person. In response to the first interrogating signal, the control circuit is configured to receive, via the transceiver, a first response signal from the medical device, the first response signal comprising an identifying information associated with one or more of the medical device and the person. The control circuit is configured to convey, via the display, the identifying information. The input device is configured to allow a user to control an operation of the scanner device.

1 Claim, 4 Drawing Sheets

(56) References Cited

U.S. PATENT DOCUMENTS

| | | |
|---|---|---|
| 2007/0232884 A1 | 10/2007 | Maschke |
| 2008/0103555 A1* | 5/2008 | Dicks ................... G16H 40/67 607/60 |
| 2008/0167531 A1* | 7/2008 | McDermott ......... A61B 5/0031 600/300 |
| 2018/0247095 A1* | 8/2018 | Sundaram ............ A61B 5/0215 |

* cited by examiner

SCANNER DEVICES FOR IDENTIFYING AND STORING INFORMATION EMITTED BY IMPLANTED MEDICAL DEVICES

CROSS-REFERENCE TO RELATED APPLICATIONS

This application claims priority to U.S. Provisional Application No. 62/740,824 filed Oct. 3, 2018, which is hereby incorporated herein by reference in its entirety.

FIELD OF THE INVENTION

The present invention relates generally to medical devices and specifically to scanner devices and methods for identifying and storing information emitted by implanted medical devices.

BACKGROUND OF THE INVENTION

Medical implants are devices or tissues that are placed inside or on the surface of the body. Many implants are prosthetics, intended to replace missing body parts. Other implants deliver medication, monitor body functions, or provide support to organs and tissues. Some implants are made from skin, bone or other body tissues. Others are made from metal, plastic, ceramic or other materials. Implants can be placed permanently, or they can be removed once they are no longer needed. For example, stents or hip implants are intended to be permanent. Over time, medical implants can move, break, or stop working properly.

Unique Device Identification ("UDI"), is a system developed and mandated by the FDA to accurately find, track, store, and manage medical devices throughout their distribution and use. Every medical device that is produced and sold in the healthcare market must be labeled with a different numeric or alphanumeric code that contains specific information about its manufacturer, expiration date, etc. Like many barcoding systems, each identifier will have two components-machine-readable, for instant computer-based recognition, and human-readable, to serve as a "two-point check" that the device is valid.

BRIEF DESCRIPTION OF THE DRAWINGS

Some of the embodiments will be described in detail, with reference to the following figures, wherein like designations denote like members, wherein.

Figure 1:
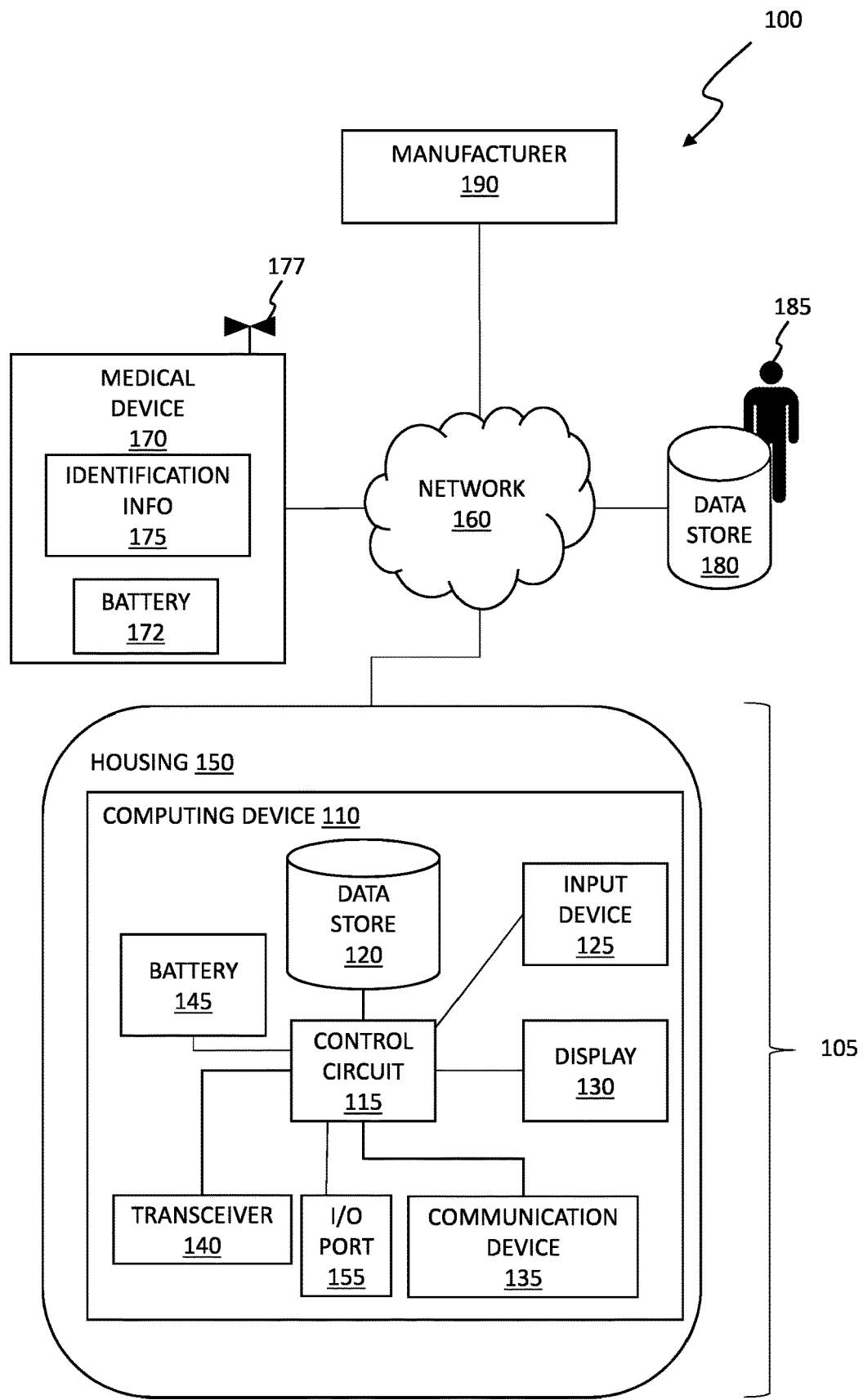
FIG. 1 depicts an environment for identifying and storing information emitted by implanted medical devices according to some embodiments.

Unless otherwise specifically noted, articles depicted in the drawings are not necessarily drawn to scale.

DETAIL DESCRIPTIONS OF THE INVENTION

All illustrations of the drawings are for the purpose of describing selected versions of the present invention and are not intended to limit the scope of any future claims related to the present invention.

Although certain embodiments are shown and described in detail, it should be understood that various changes and modifications may be made without departing from the scope of the appended claims. The scope of the present disclosure will in no way be limited to the number of constituting components, the materials thereof, the shapes thereof, the relative arrangement thereof, etc., and are disclosed simply as an example of embodiments of the present disclosure. A more complete understanding of the present embodiments and advantages thereof may be acquired by referring to the following description taken in conjunction with the accompanying drawings, in which like reference numbers indicate like features.

As a preface to the detailed description, it should be noted that, as used in this specification and the appended claims, the singular forms "a", "an" and "the" include plural referents, unless the context clearly dictates otherwise.

Embodiments disclosed herein convey scanner devices that can communicate with medically implanted devices to determine the manufacturer of the device, model number, and basic parameters.

This is important to provide timely medical care to those who arrive at a medical facility with an implanted device but are incapable of telling what device they have. Other scenarios include a pre-operative protocol where the patient's pacemaker or implantable cardioverter defibrillator ("ICD") must be identified before proceeding to the operating room. For example, anesthesiologists and surgeons require basic information on patient's pacemakers and/or defibrillators to ensure a successful surgery or procedure. Battery life, thresholds, impedances, percent pacing, and defibrillator settings are information often required before surgery. If the medical device is unknown, this can result in major delays, phone calls to vendor, and x-rays to determine the nature (Type and Model) of the implant before medical treatment can begin.

Embodiments of the instant application seek to provide scanner devices and methods for identifying and storing information emitted by implanted medical devices. FIG. 1 depicts an environment, generally 100, for identifying and storing information emitted by implanted medical devices according to some embodiments. In some embodiments, environment 100 includes scanner device 105, medical device 170, data store 180, and manufacturer 190 all in communication via network 160. Network 160 can be, for example, a local area network (LAN), a wide area network (WAN), such as the internet, a distributed computing environment, or a combination of two or more thereof, and can include wired, wireless, or fiber optic connections. Network 160 can be compatible with a variety of frequencies, such as those associated with Bluetooth®, Wi-Fi™, LTE™, cellular, radio, microwave, as well as other wireless communication protocols. In some embodiments, network 160 is a Medical Implant Communication System communication network (further discussed below). In general, network 160 can be any combination of connections and protocols that will support communications between scanner device 105, medical device 170, data store 180, and manufacturer 190.

Figure 2:
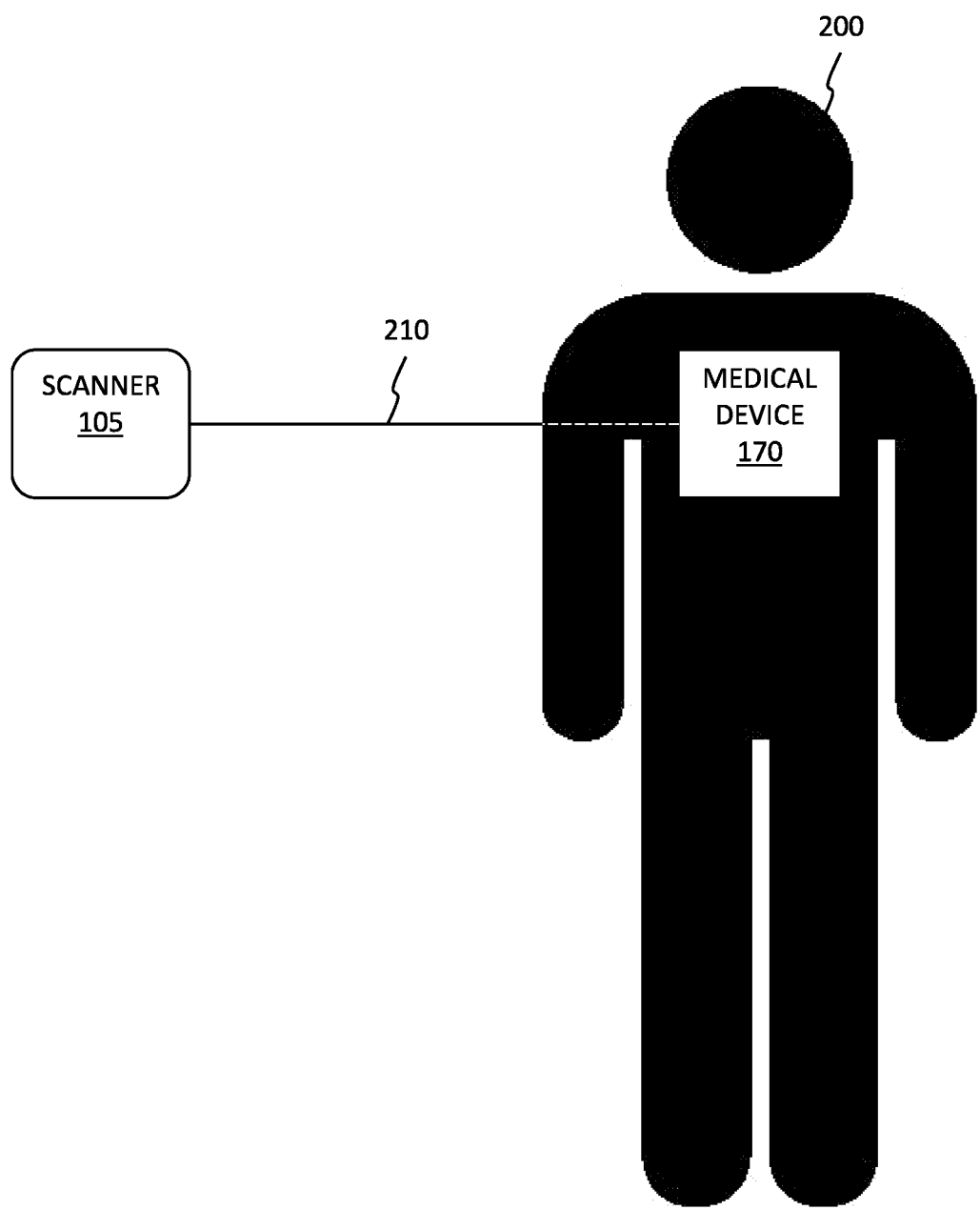
FIG. 2 illustrates the communicative relationship between a scanner device and an implanted medical device according to some embodiments.

Medical device 170 is a medical implant that is placed inside or on the surface of the body of person 200 as shown in FIG. 2. In certain embodiments, medical device 170 is a prosthetic, intended to replace a missing body part. In other aspects, medical device 170 delivers medication, monitors one or more body functions, or provides support to organs and tissues. For example, medical device 170 can diagnose, prevent, or treat diseases or other conditions, and may not carry out processes through chemical action. In some embodiments, medical device 170 is made from skin, bone or other body tissues. For example, medical device 170 can be made from metal, plastic, ceramic or other materials. Implants, such as medical device 170, can be implanted permanently or they can be removed once they are no longer needed. For example, stents or hip implants are intended to be permanent. Over time, medical implants, such as medical device 170, can move, break, or stop working properly.

Medical device 170 includes, battery 172, identification information 175 and transceiver 177. In some embodiments, identification information 175 includes the unique device identification ("UDI") of medical device 170. Transceiver 177 is a device that includes both a radio-frequency (RF) transmitter and a RF receiver. In other embodiments, transceiver 177 transmits information included in identification information 175 (e.g., to scanner device 105) in response to receiving interrogating signals via transceiver 177. For example, identification information 175 can include the unique device identification ("UDI") information of medical device 170.

In other embodiments, identification information includes information transmitted over a Medical Implant Communication System ("MICS"). MICS is a low-power, short-range, high-data-rate, 401-406 MHz communication network for transmitting data to support the diagnostic or therapeutic functions associated with medical implant devices (e.g., medical device 170). In a MICS network, implanted medical devices (e.g., medical device 170) are programmed and controlled remotely. Aspects of medical device 170 are compatible with MICS communication networks. For example, transceiver 177 can operate in the 401-406 MHz frequency band and more preferably in the 402-405 MHz.

The Internet of Medical Things ("IoMT") is an amalgamation of medical devices (e.g., medical device 170) and applications that can connect to health care information technology systems using networking technologies. IoMT can reduce unnecessary hospital visits and the burden on health care systems by connecting patients to their physicians and allowing the transfer of medical data over a secure network.

UDI is a system developed and mandated by the U.S. Food and Drug Administration ("FDA") to accurately find, track, store, and manage medical devices, such as medical device 170, throughout their distribution and use. Medical devices, such as medical device 170, that are produced and sold in the healthcare market must be labeled with a unique numeric or alphanumeric code that contains specific information about its manufacturer, expiration date, etc.

In line with such guidelines, aspects of identification information 175 include specific information about medical device 170, such its manufacturer (e.g., manufacturer 190), expiration date, version or model information, lot or batch number, serial number, expiration date, date of manufacture, the distinct identification code required by § 1271.290(c) in instances where medical device 170 is a human cell, tissue, or cellular and tissue-based product ("HCT/P"), or a combination of two or more thereof.

When a medical emergency occurs and patients with implanted medical devices arrive at a medical facility, they are often incapable of describing or defining what implanted device they have or who the manufacturer is. Current procedure is for the medical staff to call the various manufacturers that provide the implant devices to see if they have the patient's demographics listed. If they do not have the patient information listed, some form of X-Ray or scan must take place to identify the implant device. All of this may take time, and as the patient is often in distress, time is very valuable. Delays can result in more serious conditions or even death. Certain aspects of scanner device 105 provide identification information 175 (e.g., to health care professionals) to thereby facilitate the administration of healthcare services. In other embodiments, scanner device 105 is a device in an IoMT environment.

Some aspects of scanner device 105 include computing device 110 included within housing 150. Housing 150 is a rigid enclosure that protects one or more components of computing device 110. Housing 150 can include metal, metallic, polymer components, or a combination of two or more thereof. In some embodiments, housing 150 can house the components of computing device 105 in two or more communicatively coupled housings. Housing 150 constitutes, in the ideal embodiment, a physical body suitable for use in a sterile environment. Said physical body will ideally contain and define all functional physical components and user-operable controls required for operation of the handheld element of the implanted device scanner. In certain embodiments, scanner device 105 includes a first housing and a second housing. Here, the first housing includes display 130, input device 125, and control circuit 115 and the second housing includes transceiver 140.

Other aspects of computing device 110 include one or more data store 120, input device 125, display 130, communications device 135, I/O port 155, transceiver 140, battery 145 communicatively coupled via control circuit 115. For example, transceiver 140 is a device that includes both a RF transmitter and a RF receiver. In other embodiments, transceiver 140 transmits interrogating signals to and receives response signals from transceiver 177. Aspects of scanner device 105 are compatible with MICS communication networks. For example, transceiver 140 can operate in the 401-406 MHz frequency band and more preferably in the 402-405 MHz. In still other embodiments, data store 180 is an information repository accessible by healthcare professional 185. For example, data store 180 can be an offsite data storage, management, and processing component that may enable healthcare professional 185 to record and review identification information 175 captured and stored by scanner device 105.

Certain data stored in data store 180 may be anonymized in compliance with industry standards, patient instructions, or legal mandates, such as, the Health Insurance Portability and Accountability Act of 1996 ("HIPAA"). In various applications, data store 180 may serve as a central repository for the identification information for multiple instances of medical device 170. In still other embodiments, healthcare professional 185 is associated with person 200 as shown in FIG. 2, medical device 170, or both. In other embodiments, I/O port 155 is configured to provide power to battery 145 when a power source is energetically coupled to I/O port 155.

Figure 3:
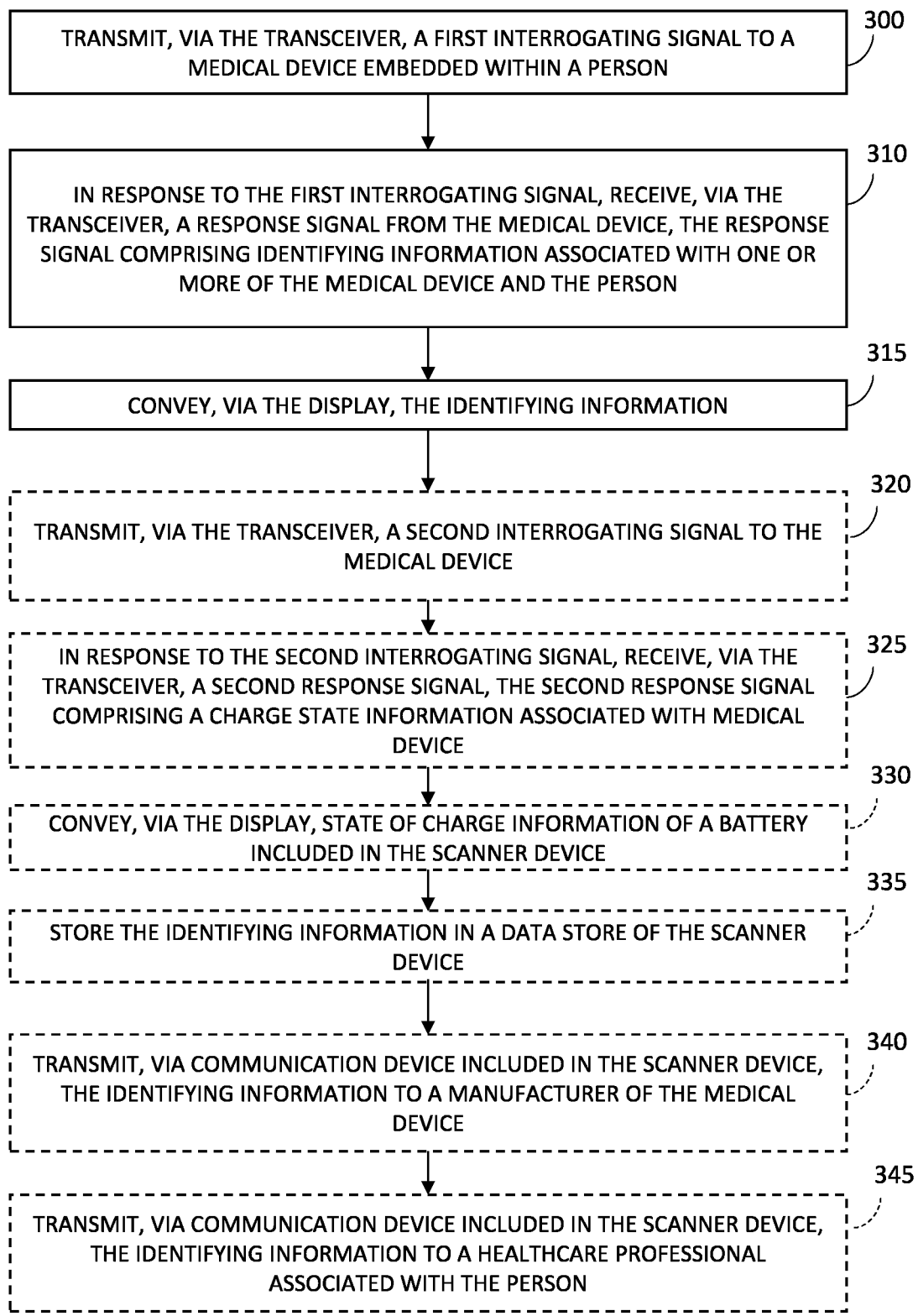
FIG. 3 is a flowchart of an operational protocol according to some embodiments.

FIG. 3 is a flowchart of an operational protocol of scanner device 105 according to some embodiments. Note that the operational protocol of FIG. 3 requires scanner device 105 and medical device 170 to be positioned proximate to each other to thereby communicate wirelessly via link 210 (as reflected in FIG. 2). For example, scanner device 105 and medical device 170 can communicate using one or more wireless communications protocols (e.g., communications protocols established by IETF, IEEE, ISO, ITU-T, etc.). Applicable wireless communications protocols include, but are not limited to, Bluetooth®, 802.11, Zigbee™, HTTP IrDA NFC, 3G, WPA, WPA2, GSM™, WEP, XML based protocols, 4G, LTE™, CDMA, and similar protocols. Control circuit 115 is configured to perform all steps, methods, protocols, and/or functions disclosed in the instant specification.

At step 300, a first interrogating signal is transmitted via transceiver 140 to medical device 105 implanted within person 200. For example, transponder 177 can receive interrogating signals from scanner device 105 and, in response, transmit response signals to scanner device 105. Input device 125 is configured to allow users to control one or more operations of scanner device 105. Input device 125 allows user to access identification information 175 stored in data store 120. At step 310, in response to the first interrogating signal, transceiver 140 receives a first response signal from medical device 170 (e.g., via transponder 177). For example, the first response signal can include identifying information 175, which is associated with medical device 170, person 200, or both. At step 315, display 130 conveys the identification information 175. For example, display 145 is an output device for presenting information (e.g., an electronic visual display, a refreshable braille display, or both)

Certain aspects of medical device 170 include battery 177 to power one or more of the functions of medical device 170. Battery 177 includes a charge state (e.g., a value representation of the level of charge of battery 177 relative to its capacity). At step 320, transceiver 140 transmits a second interrogating signal to medical device 170 (e.g., via transponder 177). At step 325, in response to the second interrogating signal, transceiver 140 receives a second response signal (e.g., via transponder 177) that includes information that reflects the charge state information associated with medical device 170 (i.e. the charge state of battery 177). At step 330, display 130 conveys the state of charge information.

At times, information about medical device 170 may need to be provided more than once. At step 335, identifying information 175 is stored in data store 120. Certain situations may require information associated with medical device 170 to be shared with its manufacturer (e.g., manufacturer 190) and associated healthcare professionals (e.g., healthcare professional 185). At step 340, scanner device transmits, via communication device 135, identifying information 175 to the manufacturer of medical device 170 (i.e. manufacturer 190). For example, communications device 135 is hardware that can transmit data, instructions, and information between scanner device 105 and receiving devices (e.g., manufacturer 190 and data store 180).

Communications device 135 can communicate wirelessly or via wired methods. At step 345, communications device 135 transmits the identifying information 175 (e.g., stored in data store 120) to a healthcare professional associated with person 200 (e.g., healthcare professional 185). For example, healthcare professional 185 accesses identification information 175 stored in data store 180.

Figure 4:
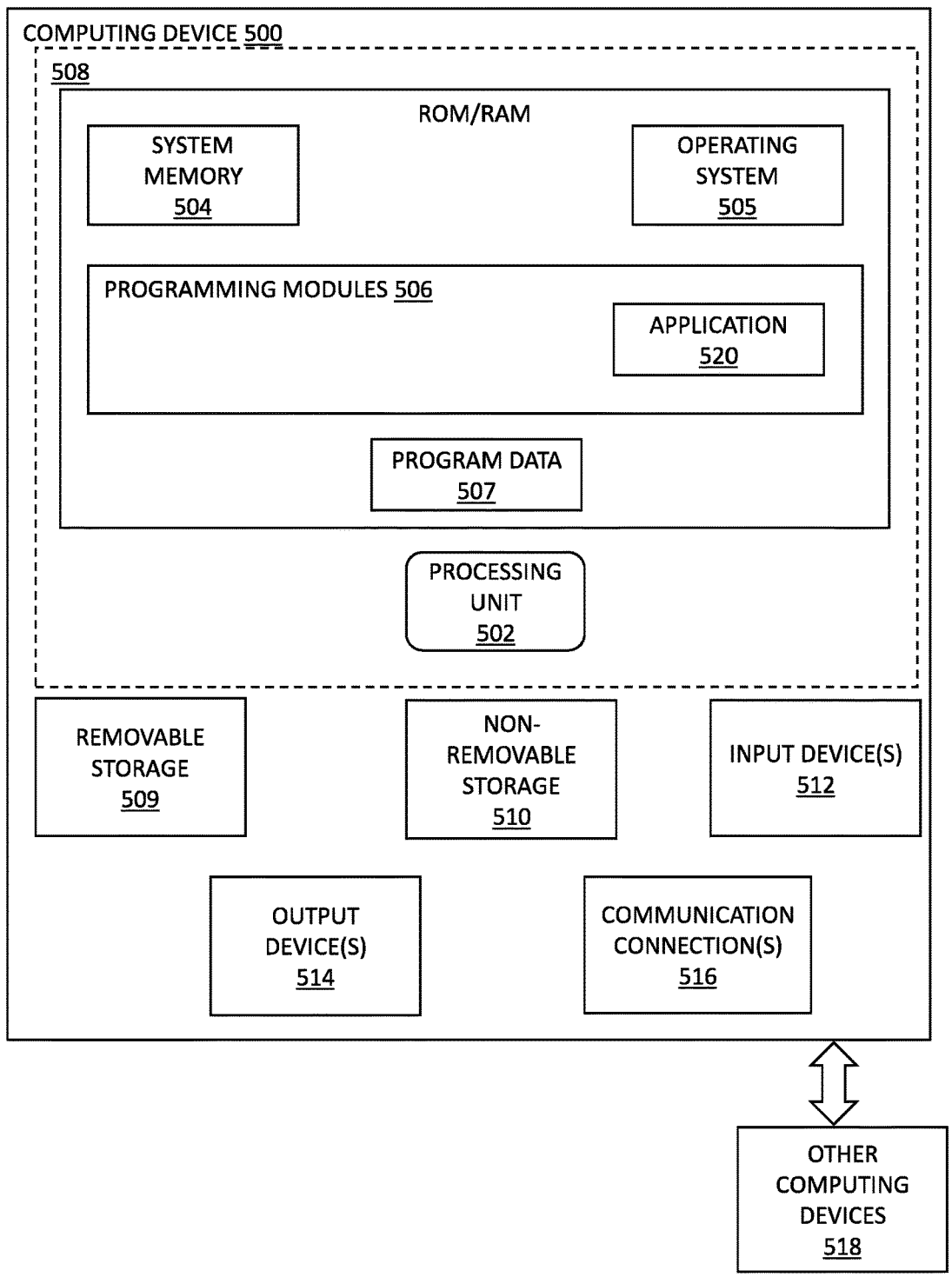
FIG. 4 depicts an exemplary system configuration according to some embodiments.

With reference to FIG. 4, a system consistent with an embodiment of the disclosure may include a computing device or cloud service, such as computing device 500. For example, computing device 110, transponder 177, as well as computing devices containing digital content information stores 130 may be represented by computing device 500. In a basic configuration, computing device 500 may include at least one processing unit 502 (e.g., control circuit 115) and a system memory 504. Depending on the configuration and type of computing device, system memory 504 may comprise, but is not limited to, volatile (e.g. random-access memory (RAM)), non-volatile (e.g. read-only memory (ROM)), flash memory, or any combination.

System memory 504 may include operating system 505, one or more programming modules 506, and may include a program data 507. In some aspects, program data 507 can include information of data store 120. Operating system 505, for example, may be suitable for controlling computing device 500's operation. In one embodiment, programming modules 506 may include image-processing module, machine learning module and/or image classifying module. Furthermore, embodiments of the disclosure may be practiced in conjunction with a graphics library, other operating systems, or any other application program and is not limited to any particular application or system. This basic configuration is illustrated in FIG. 4 by those components within a dashed line 508.

Computing device 500 may have additional features or functionality. For example, computing device 500 may also include additional data storage devices (removable and/or non-removable) such as, for example, magnetic disks, optical disks, or tape. Such additional storage is illustrated in FIG. 4 by a removable storage 509 and a non-removable storage 510. Computer storage media may include volatile and nonvolatile, removable and non-removable media implemented in any method or technology for storage of information, such as computer-readable instructions, data structures, program modules, or other data. System memory 504, removable storage 509, and non-removable storage 510 are all computer storage media examples (i.e., memory storage) that can be data store 120.

Computer storage media may include, but is not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information and which can be accessed by computing device 500. Any such computer storage media may be part of device 500. Computing device 500 may also have input device(s) 512 (e.g., input device 125) such as a keyboard, a mouse, a pen, a sound input device, a touch input device, a location sensor, a camera, a biometric sensor, etc. Output device(s) 514 such as a display (e.g., display 130), speakers, a printer, etc. may also be included. The aforementioned devices are examples and others may be used.

Computing device 500 may also contain a communication connection 516 that may allow device 500 to communicate with other computing devices 518, such as over a network in a distributed computing environment, for example, an intranet or the Internet (e.g., network 140). Communication connection 516 is one example of communication media. Communication media may typically be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media. The term computer readable media as used herein may include both storage media and communication media.

As stated above, a number of program modules and data files may be stored in system memory 504, including operating system 505. While executing on processing unit 502, programming modules 506 (e.g., application 520 such as a media player) may perform processes including, for example, one or more stages of methods, algorithms, systems, applications, servers, databases as described above. The aforementioned process is an example, and processing unit 502 may perform other processes. Other programming modules that may be used in accordance with embodiments of the present disclosure may include sound encoding/decoding applications, machine learning application, acoustic classifiers etc.

Generally, consistent with embodiments of the disclosure, program modules may include routines, programs, components, data structures, and other types of structures that may perform particular tasks or that may implement particular abstract data types. Moreover, embodiments of the disclosure may be practiced with other computer system configurations, including hand-held devices, general purpose graphics processor-based systems, multiprocessor systems, microprocessor-based or programmable consumer electronics, application specific integrated circuit-based electronics, minicomputers, mainframe computers, and the like. Embodiments of the disclosure may also be practiced in distributed computing environments where tasks are performed by remote processing devices that are linked through a communications network. In a distributed computing environment, program modules may be located in both local and remote memory storage devices.

Furthermore, embodiments of the disclosure may be practiced in an electrical circuit comprising discrete electronic elements, packaged or integrated electronic chips containing logic gates, a circuit utilizing a microprocessor, or on a single chip containing electronic elements or microprocessors. Embodiments of the disclosure may also be practiced using other technologies capable of performing logical operations such as, for example, AND, OR, and NOT, including but not limited to mechanical, optical, fluidic, and quantum technologies. In addition, embodiments of the disclosure may be practiced within a general-purpose computer or in any other circuits or systems.

Embodiments of the disclosure, for example, may be implemented as a computer process (method), a computing system, or as an article of manufacture, such as a computer program product or computer readable media. The computer program product may be a computer storage media readable by a computer system and encoding a computer program of instructions for executing a computer process. The computer program product may also be a propagated signal on a carrier readable by a computing system and encoding a computer program of instructions for executing a computer process. Accordingly, the present disclosure may be embodied in hardware and/or in software (including firmware, resident software, micro-code, etc.). In other words, embodiments of the present disclosure may take the form of a computer program product on a computer-usable or computer-readable storage medium having computer-usable or computer-readable program code embodied in the medium for use by or in connection with an instruction execution system. A computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific computer-readable medium examples (a non-exhaustive list), the computer-readable medium may include the following: an electrical connection having one or more wires, a portable computer diskette, a random-access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Embodiments of the present disclosure, for example, are described above with reference to block diagrams and/or operational illustrations of methods, systems, and computer program products according to embodiments of the disclosure. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved.

While certain embodiments of the disclosure have been described, other embodiments may exist. Furthermore, although embodiments of the present disclosure have been described as being associated with data stored in memory and other storage mediums, data can also be stored on or read from other types of computer-readable media, such as secondary storage devices, like hard disks, solid state storage (e.g., USB drive), or a CD-ROM, a carrier wave from the Internet, or other forms of RAM or ROM. Further, the disclosed methods' stages may be modified in any manner, including by reordering stages and/or inserting or deleting stages, without departing from the disclosure.

Although the invention has been explained in relation to its preferred embodiment, it is to be understood that many other possible modifications and variations can be made without departing from the spirit and scope of the invention. In other words, various embodiments may include some, none, or all of the enumerated advantages. Other technical advantages may become readily apparent to one of ordinary skill in the art after review of the following figures and description. It is intended that the present disclosure cover all possible combinations of the features shown in the different embodiments, as well as modifications and variations of the embodiments, provided they come within the scope of the claims and their equivalents.

To aid the Patent Office and any readers of any patent issued on this application in interpreting the claims appended hereto, applicants wish to note that they do not intend any of the appended claims or claim elements to invoke 35 U.S.C. 112(t) unless the words "means for" or "step for" are explicitly used in the particular claim.

What is claimed is:

1. A scanner device for identifying and storing information emitted by implanted medical devices comprising:
 a display;
 an input device;
 a transceiver;
 a control circuit communicatively coupled to the display, the input device, and the transceiver;
 a data store;
 an I/O port;
 a first housing;
 a second housing;

the first housing comprises the display, the input device, the control circuit;

the second housing comprises the transceiver;

the control circuit being configured to transmit, via the transceiver, a first interrogating signal to a medical device implanted within a person;

the medical device comprising a transceiver;

the control circuit being further configured to:

in response to the first interrogating signal, receive, via the transceiver of the scanner, a first response signal from the medical device, the first response signal comprising an identifying information associated with one or more of the medical device and the person;

transmit, via the communication device, the identifying information to a healthcare professional associated with the person carrying the medical device;

transmit, via the communication device, the identifying information to a manufacturer of the medical device;

convey, via the display, the identifying information; and wherein the input device is configured to allow a user to control an operation of the scanner device;

the medical device comprises a battery;

the battery comprises a state of charge;

the control circuit being further configured to:

transmit, via the transceiver, a second interrogating signal to the medical device;

in response to the second interrogating signal, receive, via the transceiver, a second response signal, the second response signal comprising the state of charge of the battery associated with medical device; and convey, via the display, the state of charge of the battery associated with the medical device;

wherein the control circuit is communicatively coupled to the data store; and is configured to store the identifying information in the data store;

wherein the display is configured to show data requested by the user via the input device;

wherein the I/O port is communicatively coupled to the control circuit; and wherein the I/O port is configured to provide power to the battery located inside the scanner device when a power source is energetically coupled to the I/O port; and wherein the identifying information comprises one of a model number of the medical device, a date of manufacture of the medical device, a lot number of the medical device, a serial number of the medical device, a state of charge of the battery associated with the medical device, and the distinct identification code required by § 1271.290(c) in instances where medical device is a human cell, tissue, or cellular and tissue-based product ("HCT/P").

\* \* \* \* \*